US006602400B1

(12) United States Patent
Choong et al.

(10) Patent No.: US 6,602,400 B1
(45) Date of Patent: Aug. 5, 2003

(54) METHOD FOR ENHANCED BIO-CONJUGATION EVENTS

(75) Inventors: Vi-En Choong, Chandler, AZ (US); Changming Li, Phoenix, AZ (US); Song Shi, Phoenix, AZ (US); George Maracas, Phoenix, AZ (US)

(73) Assignee: Motorola, Inc., Schaumburg, IL (US)

( * ) Notice: Subject to any disclaimer, the term of this patent is extended or adjusted under 35 U.S.C. 154(b) by 71 days.

(21) Appl. No.: 09/595,381

(22) Filed: Jun. 15, 2000

(51) Int. Cl.[7] .............................................. G01N 27/327
(52) U.S. Cl. ............... 205/777.5; 205/792; 204/403.01; 204/412
(58) Field of Search .............................. 205/775, 777.5, 205/792; 204/403.01, 412; 324/600, 658, 663, 691, 692; 435/6, 7.1, 7.2; 422/82.01, 82.02

(56) References Cited

U.S. PATENT DOCUMENTS

| 4,072,576 A | 2/1978 | Arwin et al. |
| 4,098,645 A | 7/1978 | Hartdegen et al. |
| 4,414,323 A | 11/1983 | Masuda |
| 4,683,195 A | 7/1987 | Mullis et al. |
| 4,713,347 A | 12/1987 | Mitchell et al. |
| 4,755,458 A | 7/1988 | Rabbani et al. |
| 4,840,893 A | 6/1989 | Hill et al. |
| 4,920,047 A | 4/1990 | Giaever et al. |
| 5,130,238 A | 7/1992 | Malek et al. |
| 5,164,319 A | 11/1992 | Hafeman et al. |
| 5,187,096 A | 2/1993 | Giaever et al. |
| 5,192,507 A | 3/1993 | Taylor et al. |
| 5,194,133 A | 3/1993 | Clark et al. |
| 5,312,527 A | 5/1994 | Mikkelsen et al. |
| 5,455,166 A | 10/1995 | Walker |
| 5,494,810 A | 2/1996 | Barany et al. |
| 5,519,635 A | 5/1996 | Miyake et al. |
| 5,532,128 A | 7/1996 | Eggers et al. |
| 5,540,828 A * | 7/1996 | Yacynych .............. 204/403.11 |
| 5,552,270 A | 9/1996 | Khrapko et al. |

(List continued on next page.)

FOREIGN PATENT DOCUMENTS

| WO | WO 86/05815 | 3/1985 |
| WO | WO 97/01646 A2 | 1/1997 |
| WO | WO 97/27329 | 7/1997 |
| WO | WO 97/31256 | 8/1997 |
| WO | WO 98/05424 | 2/1998 |

(List continued on next page.)

OTHER PUBLICATIONS

Bard and Faulkner, Electrochemical Methods: Fundamentals and Applications, 1980, pp. 22–26 and 316–353.*
Potyrailo et al., Anal. Chem. 70:3419–3425 (1998).
Beattie et al., "Genosensor Technology," Clinical Chemistry, 39(4): 719–722 (1993).
Cantor, C.R. et al., "Report on the Sequencing by Hybridization Workshop," Genomics, 13:1378–1383 (1992).
Commerce Business Daily Issue of Sep. 26, 1996 PSA#1688.
Drobyshev, A. et al., "Sequence Analysis by Hybridization with Oligonucleotide Microchip: Identification of β–thalassemia Mutations," Gene, 188:45–52 (1997).

(List continued on next page.)

Primary Examiner—Nam Nguyen
Assistant Examiner—Kaj K. Olsen
(74) Attorney, Agent, or Firm—Dorsey & Whitney LLP; Robin M. Silva (57) ABSTRACT

The present invention provides an apparatus and methods for efficient, high-throughput electrical or electrochemical detection of biomolecules. More specifically, the invention provides an apparatus in which an independent set of electrodes is used to increase the occurrence of a desired bio-conjugation event at a test site.

20 Claims, 4 Drawing Sheets

U.S. PATENT DOCUMENTS

| | | |
|---|---|---|
| 5,565,322 A | 10/1996 | Heller |
| 5,591,578 A | 1/1997 | Meade et al. |
| 5,595,908 A | 1/1997 | Fawcett et al. |
| 5,605,662 A | 2/1997 | Heller et al. |
| 5,632,957 A | 5/1997 | Heller et al. |
| 5,653,939 A | 8/1997 | Hollis et al. |
| 5,670,322 A | 9/1997 | Eggers et al. |
| 5,705,346 A | 1/1998 | Okamoto et al. |
| 5,705,348 A | 1/1998 | Meade et al. |
| 5,741,462 A | 4/1998 | Nova et al. |
| 5,770,369 A | 6/1998 | Meade et al. |
| 5,780,234 A | 7/1998 | Meade et al. |
| 5,787,032 A | 7/1998 | Heller et al. |
| 5,824,473 A | 10/1998 | Meade et al. |
| 5,835,404 A | 11/1998 | Heller et al. |
| 5,837,859 A | 11/1998 | Teoule et al. |
| 5,846,708 A | 12/1998 | Hollis et al. |
| 5,849,486 A | 12/1998 | Heller et al. |
| 5,849,489 A | 12/1998 | Heller |
| 5,866,345 A | 2/1999 | Wilding et al. |
| 5,891,630 A | 4/1999 | Eggers et al. |
| 5,929,208 A | 7/1999 | Heller et al. |
| 5,965,452 A | 10/1999 | Kovacs |
| 5,976,802 A | 11/1999 | Ansorge et al. |
| 6,013,166 A | 1/2000 | Heller |
| 6,017,696 A | 1/2000 | Heller |
| 6,048,690 A | 4/2000 | Heller et al. |
| 6,051,380 A | 4/2000 | Sosnowski et al. |
| 6,067,246 A | 5/2000 | Heller et al. |
| 6,068,818 A | 5/2000 | Ackley et al. |
| 6,071,394 A | 6/2000 | Cheng et al. |
| 6,096,825 A | 8/2000 | Garnier |
| 6,099,803 A | 8/2000 | Ackley et al. |
| 6,129,828 A | 10/2000 | Sheldon, III et al. |
| 6,162,603 A | 12/2000 | Heller |
| 6,207,373 B1 | 3/2001 | Sosnowski et al. |
| 6,225,059 B1 | 5/2001 | Ackley et al. |
| 6,238,624 B1 | 5/2001 | Heller et al. |
| 6,245,508 B1 | 6/2001 | Heller et al. |
| 6,249,784 B1 | 6/2001 | Macke et al. |
| 6,254,827 B1 | 7/2001 | Ackley et al. |
| 6,258,606 B1 | 7/2001 | Kovacs |
| 6,264,825 B1 | 7/2001 | Blackburn et al. |
| 6,280,590 B1 | 8/2001 | Cheng et al. |
| 6,284,117 B1 | 9/2001 | Smolko et al. |
| 6,287,517 B1 | 9/2001 | Ackley et al. |
| 6,290,839 B1 | 9/2001 | Kayyem et al. |
| 6,303,082 B1 | 10/2001 | John et al. |
| 6,306,348 B1 | 10/2001 | Havens et al. |
| 6,309,601 B1 | 10/2001 | Juncosa et al. |
| 6,309,602 B1 | 10/2001 | Ackley et al. |
| 6,315,953 B1 | 11/2001 | Ackley et al. |
| 6,319,472 B1 | 11/2001 | Ackley et al. |
| 6,331,274 B1 | 12/2001 | Ackley et al. |
| 6,375,899 B1 | 4/2002 | Ackley et al. |
| 6,379,897 B1 | 4/2002 | Weidenhammer et al. |
| 6,385,080 B1 | 5/2002 | Heller et al. |
| 6,395,493 B1 | 5/2002 | Sosnowski et al. |

FOREIGN PATENT DOCUMENTS

| | | |
|---|---|---|
| WO | WO 98/12539 A1 | 3/1998 |
| WO | WO 98/51823 | 11/1998 |
| WO | WO 99/37819 | 7/1999 |
| WO | WO 99/67425 A2 | 12/1999 |
| WO | WO 00/62931 | 10/2000 |
| WO | WO 01/35100 A2 | 5/2001 |

OTHER PUBLICATIONS

Dubiley, S. et al., "Fractionation, phosphorylation and Ligation on Oligonucleotide Microchips to Enhance Sequencing by Hybridization," Nucleic Acids Research, 25(12):2259–2265 (1997).

Elghanian et al., "Selective Colorimetric Detection of Polynucleotides Based on the Distance–Dependent Optical Properties of Gold Nanoparticles," Science, 277:1078–1081 (1997).

Griffin et al., "Single–nucleotide polymorphism analysis by MALDI–TOF mass spectrometry," Trends in Biotechnology, 14(10): 77–84 (2000).

Guschin, D. et al., "Oligonucleotide Microchips as Genosensors for Determinative and Environmental Studies in Microbiology," 63(6):2397–2402 (1997).

Hegner, et al., "Immobilizing DNA on gold via thiol modification for atomic force microscopy imaging in buffer solutions," FEBS 336(3):452–456 (1993).

Lee, et al., "Direct Measurement of the Forces Between Complementary Strands of DNA," Science, 266:771–773 (1994).

Mirkin et al., "A DNA–based Method for Ratioally Assembling Nanoparticles into Macroscopic Materials," Nature, 382:607–609 (1996).

Mirzabekov, A. et al., "Dna Sequencing by Hybridization—a Megasequencing Method and a Diagnostic Tool," Tibtech, 12:27–32 (1994).

Southern, et al., "Arrays of complementary oligonucleotides for analysing the hybridisation behaviour of nucleic acids," Nucleic Acids Research, 22(8):1368–1373 (1994).

Storhoff et al., "One–Pot Colorimetric Differentiation of Polynucleotides with Single Base Imperfections Using Gold Nanoparticles Probes," J. Am. Chem. Soc., 120:1959–1964 (1998).

Su, et al., "Interfacial Nucleic Acid Hybridization Studied by Random Primer $^{32}$P Labelling and Liquid–Phase Acoustic Network Analysis," Analytical Chemistry, 66(6):769–777 (1994).

Van Ness, J., et al., "A Versatile Solid Support System for Oligodeoxynucleotide Probe–Based Hybridization Assays," Nucleic Acids Research, 19(12):3345–3350 (1991).

Williams, et al., "Studies of oligonucleotide interactions by hybridisation to arrays: the influence of dangling ends on duplex yield," Nucleic Acids Research, 22(8):1365–1367 (1994).

\* cited by examiner

METHOD FOR ENHANCED BIO-CONJUGATION EVENTS

BACKGROUND OF THE INVENTION
1. Field of the Invention

This invention relates to the detection of biomolecules. Specifically, the invention relates to an apparatus and methods for efficient, high-throughput electrical or electrochemical detection of biomolecules. In addition, the invention relates to such apparatuses having manipulation electrodes associated with test sites for enhancing concentration or reaction of a biomolecule at a test site, with or without providing detection electrodes at the test sites. In embodiments having detection electrodes, the manipulation electrodes increase the occurrence of a desired bio-conjugation event at a test site, while the detection electrodes detect the occurrence of the desired bio-conjugation event. Methods for using the apparatuses of the invention, particularly for analysis of nucleic acids, are also provided.

2. Background of the Invention

A number of commonly-utilized biological applications, including for example, diagnoses of genetic disease, analyses of sequence polymorphisms, and studies of receptorligand interactions, rely on the ability of analytical technologies to readily detect events related to the interaction between biomolecules. These detection technologies have traditionally utilized fluorescent compounds or radioactive isotopes to monitor such interactions. For example, Potyrailo et al., 1998, *Anal. Chem.* 70: 3419–25, describe an apparatus and method for detecting interactions between immobilized fluorescently-labeled aptamers and peptides. There are, however, significant disadvantages associated with the use of radioactive or fluorescent labels to track interactions between biomolecules, including heightened health risks and increased experimental cost and complexity.

Methods for electrical or electrochemical detection of molecular interactions between biomolecules have provided an attractive alternative to detection techniques relying on radioactive or fluorescent labels. Electrical and electrochemical detection techniques are based on the detection of alterations in the electrical properties of an electrode arising from interactions between one group of molecules attached to the surface of an electrode (often referred to as "probe" molecules) and another set of molecules present in a reaction mixture (often referred to as "target" molecules) contacted with the electrode. Methods and devices related to electrical or electrochemical detection of biomolecules are disclosed in U.S. Pat. Nos. 4,072,576, 4,098,645, 4,414,323, 4,840,893, 5,164,319, 5,187,096, 5,194,133, 5,312,527, 5,532,128, 5,591,578, 5,653,939, 5,670,322, 5,705,348, 5,770,369, 5,780,234, 5,824,473, 5,891,630, 6,017,696 and International Application, Pub. No. WO 97/01646.

Electrical or electrochemical detection eliminates many of the disadvantages inherent in use of radioactive or fluorescent labels to detect interactions between the probe and target molecules. This process offers, for example, a detection technique that is safe, inexpensive, and sensitive, and is not burdened with complex and onerous regulatory requirements.

The development of microfabricated arrays of biomolecules (microarrays) has led to further improvements on traditional analytical techniques for the detection of molecular interactions between biomolecules. Microarrays of biomolecules (e.g., oligonucleotides, nucleic acids, proteins, peptides, or antibodies) have utility in a wide variety of applications in which molecular interactions between target molecules in a reaction mixture and large numbers of distinct probe molecules bound to defined regions of a substrate can be simultaneously assayed using electrical, optical, or radioactive detection strategies. Microarrays, therefore, satisfy the demand for inexpensive, high-throughput detection of biomolecular interactions.

Although microarrays have proven to be useful for high-throughput detection of molecular interactions between biomolecules, microarrays have proven to be inefficient with respect to reaction time. The probability that a particular target molecule will bind to an immobilized probe molecule is determined by the concentration of the target molecule in a reaction mixture, the diffusion rate of the target molecule, and the binding affinity of the target molecule for the immobilized probe molecule. Since target molecules in many diagnostic assays are only present in minute quantities (e.g., $<10^{-12}$ M), interactions between target molecules and immobilized probe molecules therefore occur infrequently, and reaction times of several days are not uncommon.

In recognition of the inherent inefficiency of microarrays for detecting interactions between biomolecules, several techniques for increasing the rate of molecular interactions between biomolecules (termed "bio-conjugation events" herein) have been proposed. These techniques typically involve attaching a probe molecule to an electrode, which is then electrically biased to attract the target molecule through enhancing ion migration transport. For example, U.S. Pat. No. 5,653,939 to Hollis et al. discloses a method for detecting hybridization between a target molecule in a sample solution and an oligonucleotide probe bound at a test site, wherein an electric potential is applied to an electrode comprising the test site. However, current flow through the electrode causes electrolysis at the test site, which will reduce rather than enhance bio-conjugation events at such sites.

U.S. Pat. Nos. 5,605,662; 5,632,957; and 6,017,696 to Heller et al. disclose methods for controlling molecular biological reactions in microscopic formats that utilize a self-addressable, self-assembling microelectronic apparatus. Heller et al. further provide an apparatus in which target molecules labeled with fluorescent dyes are transported by free field electrophoresis to specific test sites where the target molecules are concentrated thereby, and reacted with specific probes bound to that test site. Unbound or non-specifically interacting target molecules are thereafter removed by reversing the electric polarity at the test site. Interactions between probe and target molecules are subsequently assayed using optical means. Heller et al., however, do not suggest using their devices for electrical or electrochemical detection of molecular interactions.

There remains a need in the art to develop more efficient, high-throughput devices and methods for the detection of molecular interactions between biomolecules. In particular, there remains a need in the art to develop more efficient, high-throughput devices and methods for electrical or electrochemical detection of molecular interactions. More particularly, there remains a need in the art to develop electrical or electrochemical detection devices in which the occurrence of a desired bio-conjugation event at a test site can be favorably manipulated, thereby yielding a device with increased throughput. The development of such devices, and methods for their use, would have wide application in the medical, genetic, and molecular biological arts.

SUMMARY OF THE INVENTION

The present invention provides an apparatus and methods for efficient, high-throughput detection of bio-conjugation events occurring at a test site. The invention specifically provides apparatuses comprising a pair of manipulation electrodes at a test site to enhance occurrence of said bio-conjugation events. In particular embodiments, the apparatuses of the invention also comprise detection electrodes at a test site for electrical or electrochemical detection of bio-conjugation events occurring at the test site. In the apparatuses of the invention, the detection and manipulation electrodes are separate and distinct, and are arranged in the apparatus to avoid electrolysis at the test site. In one embodiment of the apparatuses of the invention, the arrangement of the manipulation electrodes is such that electrolysis is prevented from occurring at the manipulation electrodes. In another particular embodiment of the invention, the arrangement of the manipulation electrodes in the apparatus is such that electrolysis is allowed to occur at the manipulation electrodes.

One apparatus of the present invention comprises a supporting substrate, a test site electrode in contact with the supporting substrate, a plurality of linker moieties in contact with the test site electrode and to which probe molecules are immobilized, a pair of manipulation electrodes oriented with respect to the test site electrode to be capable of generating an electrical potential at the test site electrode and where at least one manipulation electrode is in contact with the sample solution, at least one counter-electrode in electrochemical contact with the test site electrode, a means for producing an electrical signal at the test site electrode, a means for detecting changes in the electrical signal at each test site electrode, a means for producing an electrical potential between the manipulation electrodes, and an electrolyte solution in contact with the test site electrode, linker moiety, probes, counter-electrode, and at least one of the manipulation electrodes. The test site electrode and counter-electrode are operated in a manner that prevents current flow through said electrodes, thereby avoiding electrolysis therein upon application of an electrical potential between the electrodes.

Another apparatus of the present invention comprises a supporting substrate, a plurality of test site electrodes in contact with the supporting substrate, a plurality of linker moieties in contact with the test site electrodes and to which probe molecules are immobilized, a plurality of manipulation electrode pairs oriented with respect to the test site electrodes to be capable of generating an electrical potential at the test site electrodes and where at least one manipulation electrode in each pair is in contact with the sample solution, at least one counter-electrode in electrochemical contact with the test site electrodes, a means for producing an electrical signal at each test site electrode, a means for detecting changes in the electrical signal at each test site electrode, a means for producing an electrical potential between each manipulation electrode pair, and an electrolyte solution in contact with the test site electrodes, linker moieties, probes, counter-electrode, and at least one of the manipulation electrodes in each manipulation electrode pair. The test site electrodes and counter-electrode are operated in a manner that prevents current flow through said electrodes, thereby avoiding electrolysis therein upon application of an electrical potential between the electrodes. Preferably, the probe molecules immobilized at any particular test site are identical to each other, while each test site comprises probe molecules unique to that test site.

Another apparatus of the present invention comprises a supporting substrate, a test site electrode in contact with the supporting substrate, a plurality of linker moieties in contact with the test site electrode and to which probe molecules are immobilized, a pair of manipulation electrodes oriented with respect to the test site electrode to be capable of generating an electrical potential that does not terminate at the test site electrode and where at least one manipulation electrode is in contact with the sample solution, at least one counter-electrode in electrochemical contact with the test site electrode, a means for producing an electrical signal at the test site electrode, a means for detecting changes in the electrical signal at each test site electrode, a means for producing an electrical potential between the manipulation electrodes, and an electrolyte solution in contact with the test site electrode, linker moiety, probes, counter-electrode, and at least one of the manipulation electrodes. The test site electrode and counter-electrode are operated in a manner that prevents current flow through said electrodes, thereby avoiding electrolysis therein upon application of an electrical potential between the electrodes.

Another apparatus of the present invention comprises a supporting substrate, a plurality of test site electrodes in contact with the supporting substrate, a plurality of linker moieties in contact with the test site electrodes and to which probe molecules are immobilized, a plurality of manipulation electrode pairs oriented with respect to the test site electrodes to be capable of generating an electrical potential that does not terminate at the test site electrodes and where at least one manipulation electrode in each pair is in contact with the sample solution, at least one counter-electrode in electrochemical contact with the test site electrodes, a means for producing an electrical signal at each test site electrode, a means for detecting changes in the electrical signal at each test site electrode, a means for producing an electrical potential between each manipulation electrode pair, and an electrolyte solution in contact with the test site electrodes, linker moieties, probes, counter-electrode, and at least one of the manipulation electrodes in each manipulation electrode pair. The test site electrodes and counter-electrode are operated in a manner that prevents current flow through said electrodes, thereby avoiding electrolysis therein upon application of an electrical potential between the electrodes. Preferably, the probe molecules immobilized at any particular test site are identical to each other, while each test site comprises probe molecules unique to that test site.

In some apparatuses of the present invention, the manipulation electrodes are arranged so as to prevent electrolysis from occurring at the manipulation electrodes. In other specific apparatuses of the invention, the arrangement of the manipulation electrodes is such that electrolysis is allowed to occur at the manipulation electrodes.

The apparatus of the present invention may further comprise a plurality of wells wherein each well encompasses a test site electrode to which is attached a linker moiety which is further attached to a probe molecule, at least one of the manipulation electrodes in each manipulation electrode pair, and at least one counter-electrode that is sufficient to interrogate the test site electrode in contact with linker moiety and probe molecules. The apparatus of the present invention may also further comprise at least one reference electrode. Preferably, the probe molecules in any particular well are identical to each other, while each well comprises probe molecules unique to that well.

The present invention provides methods employing the apparatus which are useful for the electrical or electrochemical detection of molecular interactions between probe molecules immobilized on (or through) linker moieties in contact with test site electrodes and target molecules in a sample solution. In one method of the present invention, a first electrical signal is detected at a test site electrode in contact with linker moieties to which probe molecules have been immobilized. Thereafter, the test site electrode is exposed to a sample mixture containing a particular target molecule, and an electrical potential is applied between a pair of manipulation electrodes oriented with respect to the test site electrode to generate an electrical potential at the test site electrode that enhances concentration of the target molecules at the test site. Preferably, the polarity of the electrical potential applied to the pair of manipulation electrodes is periodically alternated during the period that a potential is applied between the manipulation electrodes. A second electrical signal is then detected at the test site electrode in the absence of a potential at the manipulation electrodes and after a time sufficient for a biomolecular interaction to have occurred between the probe molecules immobilized at the test site electrode and target molecules in the sample mixture. The first and second electrical signals are compared, and molecular interactions between immobilized probe molecules and target molecules in the sample mixture are detected by determining that the first electrical signal is different from the second electrical signal.

In another method of the present invention, a first electrical signal is detected at a test site electrode in contact with linker moieties to which probe molecules have been immobilized. The test site electrode is exposed to a sample mixture containing a particular target molecule, an electrical potential is applied between a pair of manipulation electrodes oriented with respect to the test site electrode to generate an electric potential that does not terminate at the test site electrode, and the polarity of the electrical potential applied to the manipulation electrode pair is periodically alternated. Thereafter, a second electrical signal is detected at the test site electrode in the absence of a potential at the manipulation electrodes and after a time sufficient for a biomolecular interaction to have occurred between the probe molecules immobilized at the test site electrodes and target molecules in the sample mixture. The first and second electrical signals are then compared, and molecular interactions between immobilized probe molecules and target molecules in the sample mixture are detected by determining that the first electrical signal is different from the second electrical signal.

In still other embodiments of the methods of the present invention, target molecules in a sample mixture are labeled with an electrochemically-active reporter molecule prior to exposing the sample mixture to the test site electrode.

Specific preferred embodiments of the present invention will become evident from the following more detailed description of certain preferred embodiments and the claims.

DETAILED DESCRIPTION OF THE PREFERRED EMBODIMENTS

The apparatus and methods of the present invention are useful for the electrical or electrochemical detection of molecular interactions between probe molecules immobilized at test sites that are in electrochemical contact with electrodes and target molecules in a sample mixture. Specifically, the present invention provides an apparatus and methods for efficient, high-throughput electrical or electrochemical detection of biomolecules. More specifically, the invention provides an apparatus in which a first set of electrodes ("manipulation electrodes" or "a manipulation electrode pair") is independent from a second set of electrodes (a "test site electrode" or "detection electrode" and a counter-electrode) and is used to increase the occurrence of a desired bioconjugation event at a test site.

As used herein, the term "array" refers to an ordered spatial arrangement, particularly an arrangement of immobilized biomolecules at a plurality of test sites.

As used herein, the term "addressable array" refers to an array wherein the individual test sites have precisely defined x- and y-coordinates, so that a given test site at a particular position in the array can be identified.

As used herein, the terms "probe" and "biomolecular probe" refer to a biomolecule used to detect a complementary biomolecule. Examples include antigens that detect antibodies, oligonucleotides that detect complimentary oligonucleotides, and ligands that detect receptors. Such probes are preferably immobilized at a test site in electrochemical contact with an electrode comprising a substrate, and optionally a linker moiety.

As used herein, the terms "bioarray," "biochip" and "biochip array" refer to an ordered spatial arrangement of immobilized biomolecules at test sites each independently in electrochemical contact with a plurality of electrodes arrayed on a solid supporting substrate. Preferred probe molecules include nucleic acids, oligonucleotides, peptides, ligands, antibodies and antigens; oligonucleotides are the most preferred probe species. Biochips, as used in the art, encompass substrates containing arrays or microarrays, preferably ordered arrays and most preferably ordered, addressable arrays, of biological molecules that comprise one member of a biological binding pair. Typically, such arrays are oligonucleotide arrays comprising a nucleotide sequence that is complementary to at least one sequence that may be or is expected to be present in a biological sample. Alternatively, proteins, peptides or other small molecules can be arrayed in such biochips for performing, inter alia, immunological analyses (wherein the arrayed molecules are antigens) or assaying biological receptors (wherein the arrayed molecules are ligands, agonists or antagonists of said receptors).

In the apparatuses of the present invention, the detection and manipulation electrodes are separate and distinct, and are arranged in the apparatus to avoid electrolysis at the test site. In one embodiment of the apparatuses of the invention, the orientation of the manipulation electrodes with respect to the electrolyte prevents electrolysis from occurring at the manipulation electrodes. For example, in one such embodiment, the manipulation electrodes are arranged in the apparatus wherein one of the manipulation electrodes is not contacting the sample solution. In another such embodiment, one of the manipulation electrodes is insulated to isolate said electrode from the sample solution. This can be accomplished, for example, by embedding the electrode in the supporting substrate or by coating the electrode with an isolation layer such as non-conductive polymers or paint.

In alternative embodiments of the apparatuses of the invention, the orientation of the manipulation electrodes with respect to the electrolyte permits electrolysis to occur at the manipulation electrodes. In this embodiment, the manipulation electrodes are designed so that one manipulation electrode will have a much larger surface area than the other manipulation electrode. Furthermore, in this embodiment, the manipulation electrodes are arranged in the apparatus in such a way that the electrode having the larger surface area is located closer to the test site electrode and the electrode having the smaller surface area is located at least one order of magnitude farther from the test site electrode. No electrolysis will occur at the manipulation electrode having the larger surface area since the polarization of this electrode will be very small when a manipulation voltage is superimposed across the manipulation electrodes. Although electrolysis may occur at the manipulation electrode having the smaller surface area, it will not interfere with the detection of bio-conjugation events at the test site due to its distance from the test site.

In one embodiment of the present invention, the apparatus comprises a supporting substrate, a test site electrode in contact with the supporting substrate, a plurality of linker moieties in contact with the test site electrode and to which probe molecules are immobilized, a pair of manipulation electrodes oriented with respect to the test site electrode to be capable of generating an electrical potential at the test site electrode and where at least one manipulation electrode is in contact with the sample solution, at least one counter-electrode in electrochemical contact with the test site electrode, a means for producing an electrical signal at the test site electrode, a means for detecting changes in the electrical signal at each test site electrode, a means for producing an electrical potential between the manipulation electrodes, and an electrolyte solution in contact with the test site electrode, linker moiety, probes, counterelectrode, and at least one of the manipulation electrodes. The test site electrode and counterelectrode are preferably operated in a manner that avoids current flow and hence electrolysis of the probe or target molecules. Advantageously, this manner of operation dispenses with the need to supply a permeation or other protective layer on the test site electrode.

In an alternative embodiment of the present invention, the apparatus comprises a supporting substrate, a plurality of test site electrodes in contact with the supporting substrate, a plurality of linker moieties in contact with the test site electrodes and to which probe molecules are immobilized, a plurality of manipulation electrode pairs oriented with respect to the test site electrodes to be capable of generating an electrical potential at the test site electrodes and where at least one manipulation electrode in each pair is in contact with the sample solution, at least one counter-electrode in electrochemical contact with the test site electrodes, a means for producing an electrical signal at each test site electrode, a means for detecting changes in the electrical signal at each test site electrode, a means for producing an electrical potential between each manipulation electrode pair, and an electrolyte solution in contact with the test site electrodes, linker moieties, probes, counter-electrode, and at least one of the manipulation electrodes in each manipulation electrode pair. Each test site electrode and counter-electrode pair is preferably operated in a manner that avoids current flow and hence electrolysis of the probe or target molecules at the test site. Preferably, the probe molecules in any particular test site are identical to each other (for example, in oligonucleotide embodiments of the apparatus, probe molecules at a test site all have the same sequence), while each test site comprises probe molecules unique to that test site (i.e., the sequence of the oligonucleotide probe molecules in different test sites are different).

In another embodiment of the present invention, the apparatus comprises a supporting substrate, a test site electrode in contact with the supporting substrate, a plurality of linker moieties in contact with the test site electrode and to which probe molecules are immobilized, a pair of manipulation electrodes oriented with respect to the test site electrode to be capable of generating an electrical potential that does not terminate at the test site electrode and where at least one manipulation electrode is in contact with the sample solution, at least one counter-electrode in electrochemical contact with the test site electrode, a means for producing an electrical signal at the test site electrode, a means for detecting changes in the electrical signal at each test site electrode, a means for producing an electrical potential between the manipulation electrodes, and an electrolyte solution in contact with the test site electrode, linker moiety, probes, counter-electrode, and at least one of the manipulation electrodes. The test site electrode and counter-electrode are preferably operated in a manner that avoids current flow and hence electrolysis of the probe or target molecules.

In still another embodiment of the present invention, the apparatus comprises a supporting substrate, a plurality of test site electrodes in contact with the supporting substrate, a plurality of linker moieties in contact with the test site electrodes and to which probe molecules are immobilized, a plurality of manipulation electrode pairs oriented with respect to the test site electrodes to be capable of generating an electrical potential that does not terminate at the test site electrodes and where at least one manipulation electrode in each pair is in contact with the sample solution, at least one counter-electrode in electrochemical contact with the test site electrodes, a means for producing an electrical signal at each test site electrode, a means for detecting changes in the electrical signal at each test site electrode, a means for producing an electrical potential between each manipulation electrode pair, and an electrolyte solution in contact with the test site electrodes, linker moieties, probes, counter-electrode, and at least one of the manipulation electrodes in each manipulation electrode pair. Each test site electrode and counter-electrode pair is preferably operated in a manner that avoids current flow and hence electrolysis of the probe or target molecules at the test site.

The supporting substrate of the apparatus of the invention is advantageously made from any solid material, including but not limited to glass, silicon, plastic, rubber, fabric, ceramics, printed circuit board, or combinations thereof. In preferred embodiments, the supporting substrate of the apparatus of the present invention is composed of silicon or glass. Test site electrodes and manipulation electrode pairs are embedded within or placed in contact with the supporting substrate. The supporting substrate has a surface area between about 0.01 $\mu m^2$ and about 5 $cm^2$ containing from 1 to about $10^8$ test site electrodes and manipulation electrode pairs. In a preferred embodiment, the supporting substrate has a surface area of about 10,000 $\mu m^2$ and contains about $10^4$ test site electrodes and manipulation electrode pairs. In preferred embodiments, the test site electrodes are arranged on the supporting substrate so that they are separated by a distance of from about 0.05 $\mu m$ to 0.5 mm. In more preferred embodiments, the test site electrodes are regularly spaced on the solid supporting substrate with a uniform spacing there between. Preferably, the probe molecules in any particular test site are identical to each other, while each test site comprises probe molecules unique to that test site.

In some embodiments of the present invention, test site electrodes project from the surface of the substrate, with Such projections extending from about $5 \times 10^{-8}$ to about $1 \times 10^{-5}$ cm from the surface of the supporting substrate. In other embodiments, the test site electrodes comprise a flat disk of conductive material that is embedded in the supporting substrate and is exposed at the substrate surface, with the supporting substrate acting as an insulator in the spaces between the test site electrodes.

In some embodiments of the present invention, manipulation electrode pairs project from the surface of the substrate, with such projections extending from about $5 \times 10^{-8}$ to about $1 \times 10^{-5}$ cm from the surface of the supporting substrate. In other embodiments, the manipulation electrode pairs comprise flat disks of conductive material that are embedded in the supporting substrate and exposed at the substrate surface, with the supporting substrate acting as an insulator in the spaces between the manipulation electrode pairs. The manipulation electrodes are preferably separated by a distance of from about 100 nm to about 1 cm, and more preferably by a distance of from about 1 $\mu$m to about 500 $\mu$m. In some embodiments of the present invention, the manipulation electrodes are configured with respect to a test site electrode so that an electrical potential applied to the manipulation electrodes generates an electric field having lines-of-force that terminate at the test site electrode. In other embodiments, the manipulation electrodes are configured with respect to the test site electrode so that an electrical potential applied to the manipulation electrodes generates an electric field having lines-of-force that do not terminate at the test site electrode. In still other embodiments, the manipulation electrodes are configured so that, if the electrical polarity at the manipulation electrode pair is periodically alternated, target molecules in the sample mixture will repeatedly traverse the test site electrode.

For example, a manipulation electrode positioned proximately to or underneath the test site electrode will produce electric field lines of force terminating at the test site electrode thereby concentrating electrically-charged target molecules at the test site electrode and repulsing or removing such electrically-charged target molecules that are not bound to probes attached to the test site electrode when the polarity of the electric field lines of force are reversed. Alternatively, manipulation electrodes positioned perpendicular to the test site electrode can "stir" the electrically-charged target molecules across the surface of the test site electrode when the polarity of the electric field lines of force is rapidly oscillated. Other advantageous geometric orientations of the manipulation electrodes relative to the test site electrode will be understood by those with skill in the art.

Figure 1A:
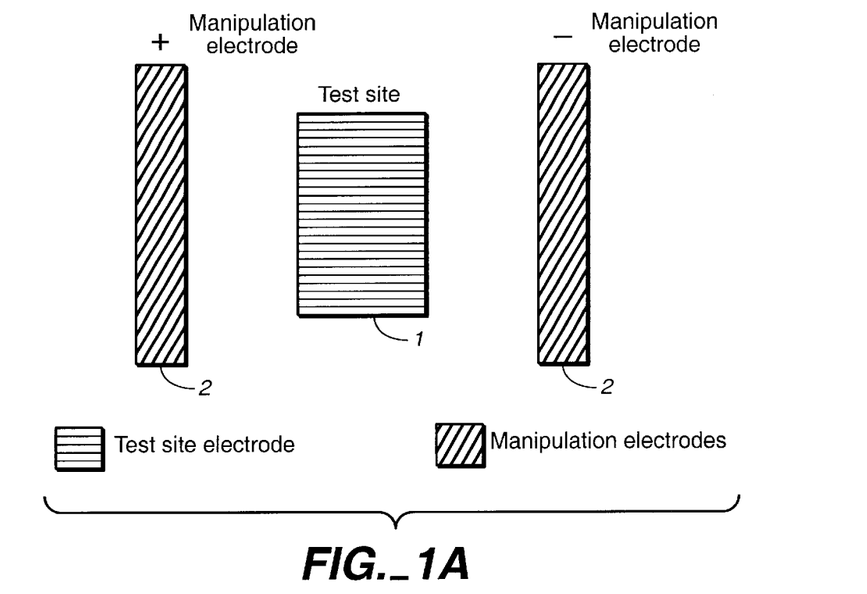
FIGS. 1A–1B illustrate schematic representations of the top view of two-electrode embodiments of the apparatus of the invention.
Figure 1B:
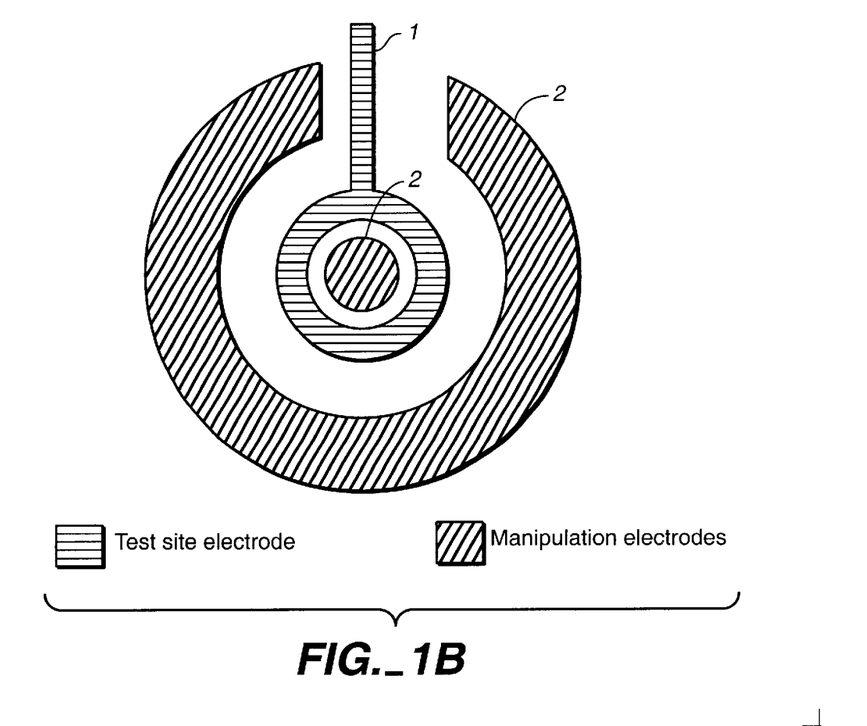
Figure 2A:
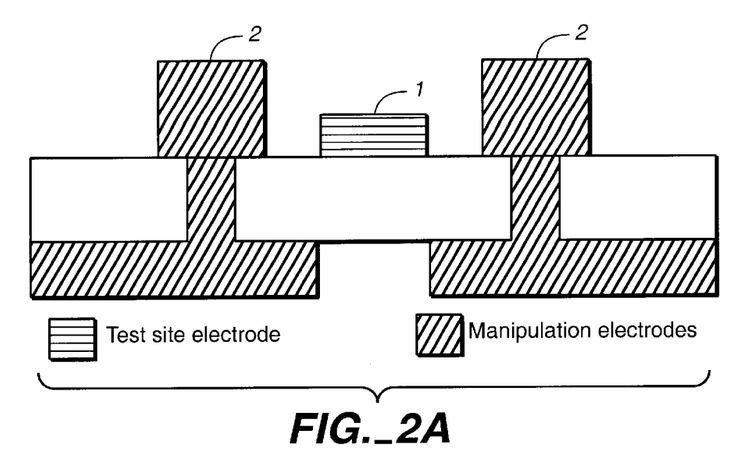
FIGS. 2A–2I illustrate schematic representations of the side view of three-electrode embodiments of the apparatus of the invention.
Figure 2B:
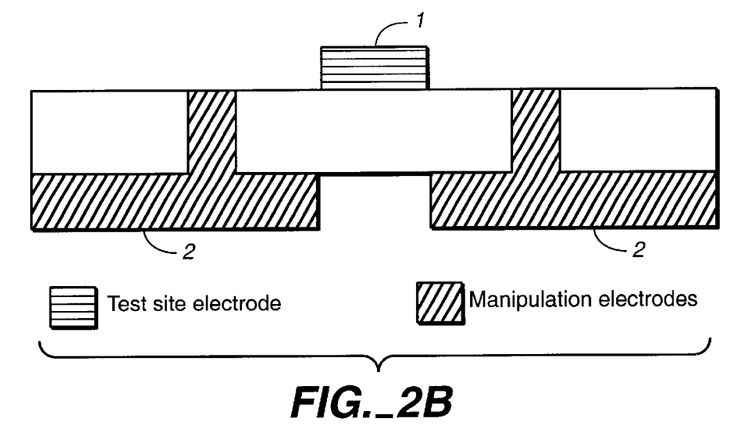
Figure 2C:
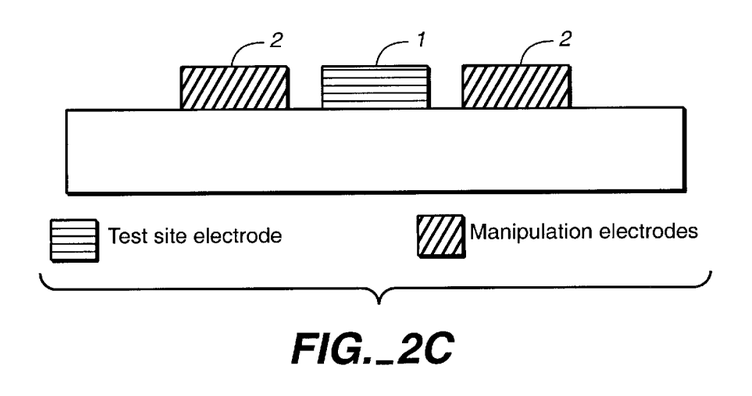
Figure 2D:
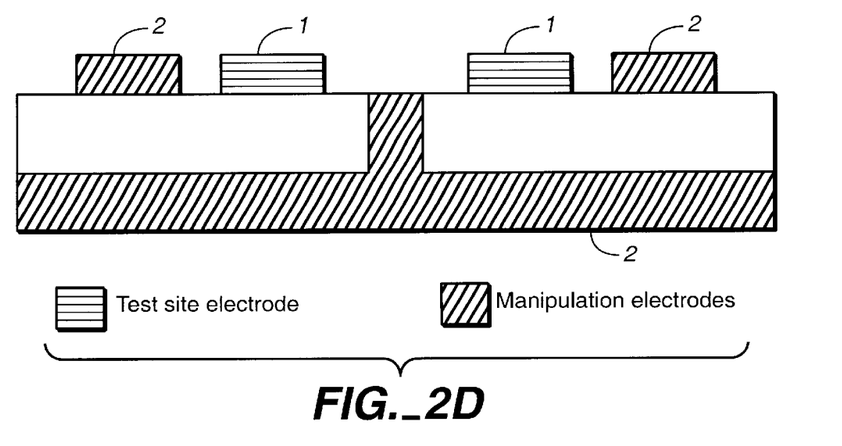
Figure 2E:
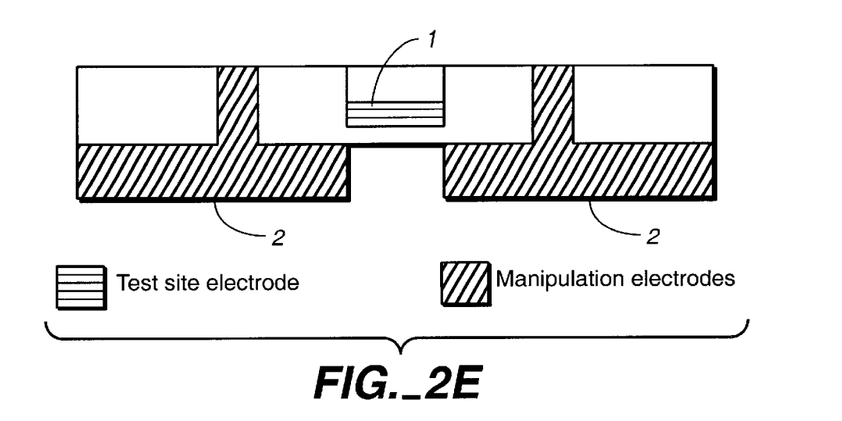
Figure 2F:
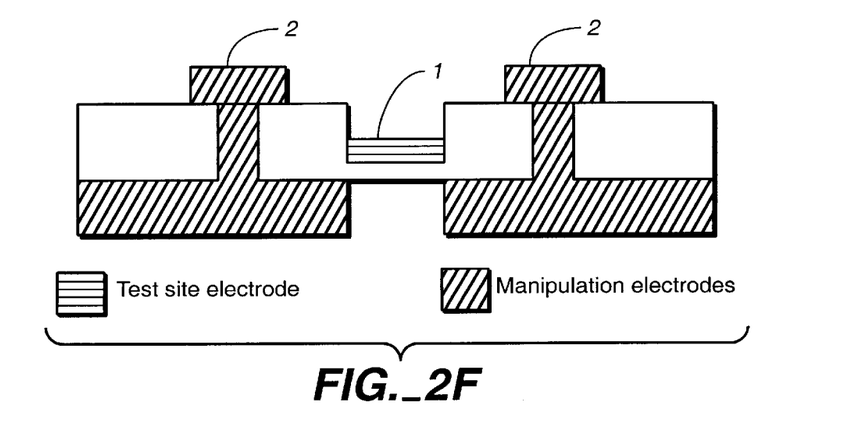
Figure 2G:
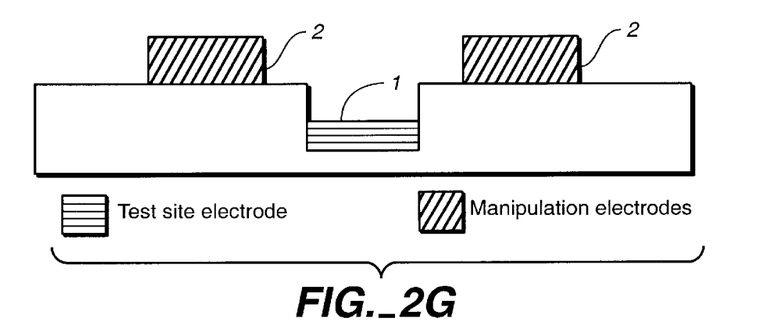
Figure 2H:
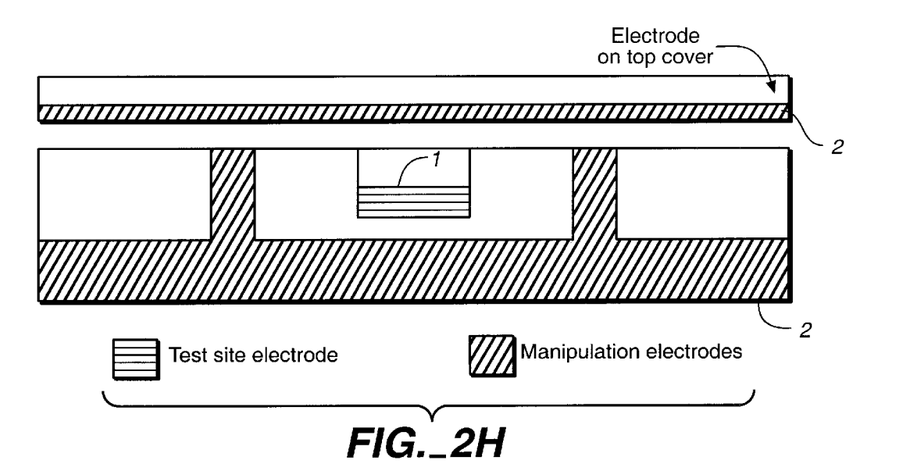
Figure 2I:
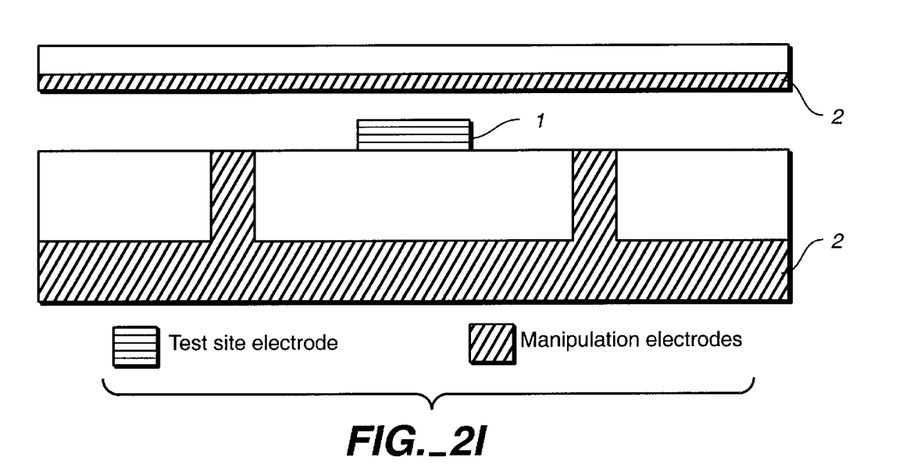

FIGS. 1A–1B illustrate schematic representations of the top view of embodiments of the apparatus of the invention comprising a test site electrode 1 and manipulation electrode pair 2. FIGS. 2A–2I illustrate schematic representations of the side view of embodiments of the apparatus of the invention comprising a test site electrode 1, and a manipulation electrode pair 2.

In the preferred embodiment of the present invention the test site electrodes comprise a gold or platinum conductor and a glass or silicon insulator. In alternative embodiments, the test site electrodes comprise conductor substances such as solid or porous foils or films of silver, titanium, copper, chromium, or aluminum, or metal oxides, metal nitrides, metal carbides, carbon, graphite, conductive plastic (such as polythiophenes, polyanilines, or polypyrroles), metal impregnated polymers, or combinations thereof. In additional embodiments, the test site electrodes comprise substrate and/or insulator substances such as plastic, rubber, fabric, ceramics, printed circuit board, or combinations thereof. The test site electrodes of the present invention preferably have an exposed conductive surface of from about 0.01 $\mu$m$^2$ to 0.5 cm$^2$. In the preferred embodiment, the exposed conductive material has an area of from about 100 to 160,000 $\mu$m$^2$.

In a preferred embodiment of the present invention manipulation electrode pairs comprise a gold or platinum conductor and a glass or silicon insulator. In alternative embodiments, the manipulation electrodes pairs comprise conductor substances such as solid or porous foils or films of silver, titanium, copper, chromium, or aluminum, or metal oxides, metal nitrides, metal carbides, carbon, graphite, conductive plastic, metal impregnated polymers, or combinations thereof. In additional embodiments, the manipulation electrode pairs comprise substrate andlor insulator substances such as plastic, rubber, fabric, ceramics, printed circuit board, or combinations thereof. The manipulation electrode pairs of the present invention preferably have an exposed conductive surface of from about 0.01 $\mu$m$^2$ to 0.5 cm$^2$. In the preferred embodiment, the exposed conductive material has an area of from about 100 to 160,000 $\mu$m$^2$. The manipulation electrodes are preferably oriented in the test site so that a potential applied across the electrodes enhances or diminishes the concentration of a target molecule at the test site, specifically at the test site electrode.

The apparatus of the present invention comprises at least one counter-electrode. In a preferred embodiment of the present invention the counter-electrode comprises a conductive material, with an exposed surface that is significantly larger than that of the test site electrodes. In a preferred embodiment, the counter electrode comprises platinum wire. In alternative embodiments, the counter-electrode comprises solid or porous films of gold, silver, platinum, titanium, copper, chromium, or aluminum, or metal oxides, metal nitrides, metal carbides, carbon, graphite, conductive plastic, metal impregnated polymers, or combinations thereof.

In other embodiments of the present invention, the apparatus comprises at least one reference electrode. The reference electrode is used in assays where an estimate or determination of the number or concentration of target molecules in a sample solution is desired. In preferred embodiments, the reference electrode comprises a silver/silver chloride electrode. In alternative embodiments, the reference electrode comprises solid or porous films of gold, platinum, titanium, copper, chromium, or aluminum, or metal oxides, metal nitrides, metal carbides, carbon, graphite, conductive plastic, metal impregnated polymers, or combinations thereof.

In still other embodiments of the present invention, the apparatus further comprises a plurality of wells wherein each well encompasses a test site electrode to which is attached a linker moiety which is further attached to a probe molecule, at least one of the manipulation electrodes in each manipulation electrode pair, and at least one counter-electrode that is sufficient to interrogate the test site electrode in contact with linker moiety and probe molecules. The term "wells" is used herein in its conventional sense, to describe a portion of the supporting substrate in which the test site electrode, counter-electrode, and at least one manipulation electrode are contained in a defined volume; said wells can protrude from the surface of the supporting substrate, or be embedded therein.

In some embodiments of the present invention, the linker moieties of the apparatus are composed of materials including, but not limited to, polyacrylamide gel, agarose gel, polyethylene glycol, cellulose gel, or sol gel. In one preferred embodiment, the linker moieties comprise polyacrylamide gel. In alternative embodiments of the present invention, the linker moieties comprise a conjugated polymer or copolymer film. Such conjugated polymer or copolymer film is composed of materials including, but not limited to, polypyrrole, polythiphene, polyaniline, polyfuran, polypyridine, polycarbazole, polyphenylene, poly (phenylenvinylene), polyfluorene, or polyindole, or their derivatives, copolymers, or combinations thereof. In another preferred embodiment, the linker moieties comprise a neutral pyrrole matrix. In still other embodiments, the linker moieties comprise thiol linkers.

The biological molecules of the invention (both probe molecules and target molecules) carry an electrical charge in aqueous solution under appropriate conditions of hydrogen ion concentration and dissolved salts; said conditions are generally determined in part by the composition of the biological sample and the electrolyte solution. In preferred embodiments of the present invention, the probe molecules are nucleic acids, oligonucleotides, or combinations thereof. Oligonucleotide probe molecules preferably comprise from about 10 to about 100, more preferably from about 10 to about 50, and most preferably from about 15 to about 30, nucleotide residues. Nucleic acid probe molecules comprise from about 10 to about 5000 basepairs, more preferably from about 100 to about 1000 basepairs, and most preferably from about 200 to about 500 basepairs. In a particular embodiment of the present invention, the probe molecules are aptamers (i.e., oligonucleotides capable of interacting with target molecules such as peptides). Oligonucleotide or nucleic acid probe molecules can be immobilized on linker moieties (or immobilized on test site electrodes via linker moieties) using techniques known to those with skill in the art, wherein said immobilization does not interfere with or inhibit the ability of the probe molecules to interact with nucleic acid target molecules in the sample mixture.

In alternative preferred embodiments of the present invention, the probe molecules of the apparatus comprise proteins or peptides. The protein or peptide probe molecules of the present invention preferably comprise from about 5 to about 500 amino acid residues, and are immobilized on linker moieties using techniques known to those with skill in the art, wherein said immobilization does not interfere with or inhibit the ability of the probe molecules to interact with target molecules in the sample mixture. In one preferred embodiment, the probes are antibodies. The antibodies immobilized on the linker moieties of the apparatus of the invention may be polyclonal or monoclonal antibodies, or F(ab) fragments, F(ab)' fragments, F(ab)$_2$ fragments, or F$_v$ fragments of polyclonal or monoclonal antibodies, or F(ab) or single chain antibodies selected from in vitro libraries.

In still other embodiments of the present invention, the probe molecules comprise a natural products library, a phage display library, or a combinatorial library known to those with skill in the art.

Electrochemical contact between the test site electrodes, linker moieties, probe molecules, counter-electrode, at least one of the manipulation electrodes in a manipulation electrode pair, and/or the reference electrode is advantageously provided using an electrolyte solution in contact with each of these components. Electrolyte solutions useful in the apparatus and methods of the invention include any electrolyte solution at physiologically-relevant ionic strength (equivalent to about 0.15 M NaCl) and neutral pH. Examples of electrolyte solutions useful with the apparatus and methods of the invention include but are not limited to phosphate buffered saline, HEPES buffered solutions, and sodium bicarbonate buffered solutions.

In preferred embodiments of the present invention, molecular interactions between immobilized probe molecules and target molecules in a sample mixture are detected by detecting an electrical signal using AC impedance. In other embodiments, such molecular interactions are detected by detecting an electrical signal using an electrical detection method selected from the group consisting of impedance spectroscopy, cyclic voltammetry, AC voltammetry, pulse voltammetry, square wave voltammetry, AC voltammetry, hydrodynamic modulation voltammetry, conductance, potential step method, potentiometric measurements, amperometric measurements, current step method, other steady-state or transient measurement methods, and combinations thereof. In common among the various methods for detecting molecular interactions between probe and target molecules is the feature that current flow through the test site electrodes is minimized to avoid electrolysis of the electrochemically labile probe and target molecules at the electrode surface.

In one embodiment of the apparatus of the present invention, the means for producing electrical impedance at each test electrode is accomplished using a Model 1260 Impedance/Gain-Phase Analyzer with Model 1287 Electrochemical Interface (Solartron Inc., Houston, Tex.). Other electrical impedance measurement means include, but are not limited to, transient methods using AC signal perturbation superimposed upon a DC potential applied to an electrochemical cell such as AC bridge and AC voltammetry. The measurements can be conducted at any particular frequency that specifically produces electrical signal changes that are readily detected or otherwise determined to be advantageous. Such particular frequencies are advantageously determined by scanning frequencies to ascertain the frequency producing, for example, the largest difference in electrical signal. The means for detecting changes in impedance at each test site electrode as a result of molecular interactions between probe and target molecules can be accomplished by using any of the above-described instruments. The means for producing an electrical field at each manipulation electrode pair may also be accomplished by using any of the above-described instruments and analytical methods.

The present invention also provides methods that are useful for the electrical or electrochemical detection of molecular interactions between target molecules in a sample solution and probe molecules immobilized on (or attached thereto using) linker moieties bound to, in contact with, or covalently attached to test site electrodes.

In one embodiment of the methods of the present invention, molecular interactions between probe and target molecules are detected by detecting a first electrical signal at a test site electrode to which probe molecules have been immobilized, preferably via linker moieties; exposing the test site to a sample mixture containing a particular target molecule; applying an electrical potential between a pair of manipulation electrodes oriented with respect to the test site to generate an electric field having lines-of-force that terminate at the test site electrode; and detecting a second electrical signal at the test site electrode. The first and second electrical signals are then compared, and molecular interactions between immobilized probe molecules and target molecules in the sample mixture are detected by determining that the first electrical signal is different from the second electrical signal. By generating an electric field having lines-of-force that terminate at the test site electrode, the effective concentration of target molecules in the sample in the vicinity of the test site is increased, and the occurrence of desired bio-conjugation events between immobilized probe molecules and target molecules in the sample mixture is thereby increased.

By applying the potential between the manipulation electrodes, the effective concentration of target molecules in the sample solution in the vicinity of the test site electrode is increased. By periodically alternating the polarity of the electrical potential applied between the manipulation electrode pair, the target molecules are forced to traverse the test site electrode to which probe molecules are immobilized, and the occurrence of desired bio-conjugation events between immobilized probe molecules and target molecules in the sample mixture is thereby increased. Generally, the electrical signal detected at the test site electrode will increase with hybridization of nucleic acids when using amperometric detection methods. When using impedance methods, however, the changes in the electrical signal detected at the test site electrode will depend on the types of molecules being detected, he surface charge of these molecules, and whether there have been interactions between these molecules at the test site.

In another embodiment of the methods of the present invention, molecular interactions between probe and target molecules are detected by detecting a first electrical signal at a test site electrode to which probe molecules have been immobilized, preferably via a linker moiety; exposing the test site to a sample mixture containing a particular target molecule; applying an electrical potential between a pair of manipulation electrodes oriented with respect to the test site to generate an electric field having lines-of-force that do not terminate at the test site electrode and oscillating the polarity of the electrodes; and detecting a second electrical signal at the test site electrode. The first and second electrical signals are then compared, and molecular interactions between immobilized probe molecules and target molecules in the sample mixture are detected by determining that the first electrical signal is different from the second electrical signal. By generating an electric field having lines-of-force that do not terminate at the test site electrode, the manipulation electrodes can be used to "stir" the sample solution, increasing the interactions between target molecules within the sample solution and immobilized probe molecules.

In some embodiments of the methods of the present invention, detection of molecular interactions between probe and target molecules is accomplished or enhanced by the coupling of an electrochemically-active moiety (termed a "reporter group") to the target molecule. Target molecules labeled with electrochemically-active reporters useful in the methods of the present invention are electrochemically-active, i.e., they are capable of participating in oxidation/reduction (redox) reactions under an applied voltage potential that can be achieved under conditions that are compatible with the biological molecules comprising the microelectrodes in contact with linker moieties and target molecule-containing sample mixtures of the invention. Target molecules labeled with an electrochemically-active moiety useful in the methods of the present invention may be prepared by labeling suitable target molecules with any reporter group having an electrochemically-distinctive property, most preferably an oxidation/reduction potential that can be distinguished from other components of the binding reaction, and that does not interfere with the molecular interaction to be detected. In preferred embodiments of the method of the present invention, target molecules are labeled with electrochemical reporter groups comprising a transition metal complex, most preferably containing a transition metal ion that is ruthenium, cobalt, iron, zinc, nickel, magnesium, or osmium.

In other embodiments of the present invention, target molecules are labeled with the following non-limiting examples of electrochemically-active moieties:

Redox moieties useful against an aqueous saturated calomel reference electrode include: 1,4-benzoquinone, ferrocene, tetracyanoquinodimethane, N,N,N',N'-tetramethyl-p-phenylenediamine, or tetrathiafulvalene.

Redox moieties useful against an Ag/AgCl reference electrode include: 9-aminoacridine, acridine orange, aclarubicin, daunomycin, doxorubicin, pirarubicin, ethidium bromide, ethidium monoazide, chlortetracycline, tetracycline, minocycline, Hoechst 33258, Hoechst 33342, 7-aminoactinomycin D, Chromomycin $A_3$, mithramycin A, Vinblastine, Rifampicin, $Os(bipyridine)_2(dipyridophenazine)_2^+$, $Co(bipyridine)_3^{3+}$, or Fe-bleomycin.

The electrochemically-active moiety comprising the electrochemically-active reporter-labeled target molecule used in certain embodiments of the methods of the present invention is optionally linked to the target molecule through a linker, preferably having a length of from about 10 to about 20 Angstroms. The linker can be an organic moiety such as a hydrocarbon chain $(CH_2)_n$ (where n is an integer from 1 to about 20), or can comprise an ether, ester, carboxyamide, or thioether moiety, or a combination thereof. The linker can also be an inorganic moiety such as siloxane (O—Si—O). The length of the linker is selected so that the electrochemically-active moiety does not interfere with the molecular interaction to be detected.

It should be understood that the foregoing disclosure emphasizes certain specific embodiments of the invention and that all modifications or alternatives equivalent thereto are within the spirit and scope of the invention as set forth in the appended claims.

What we claim is:

1. A method for the electrical or electrochemical detection of molecular interactions between an immobilized probe molecule and a target molecule, comprising:

(a) providing a substrate comprising at least one test site electrode comprising immobilized probe molecules;

(b) contacting said test site electrode with a sample mixture containing a particular target molecule;

(c) concentrating said target molecules by applying an electrical potential between a pair of manipulation electrodes such that bioconjugation between said immobilized probe molecules and said target molecule is enhanced, and wherein said bioconjugation forms a conjugated complex, wherein said conjugated complex does not comprise a reporter group;

(d) detecting an electrical signal at said test site electrode; and (e) determining whether said target molecule is present.

2. The method of claim 1 wherein said detection is an electrical detection method selected from the group consisting of impedance spectroscopy, AC impedance, cyclic voltammetry, AC voltammetry, pulse voltammetry, square wave voltammetry, hydrodynamic modulation voltammetry, conductance, potential step method, potentiometric measurements, amperometric measurements, and current step method.

3. A method according to claim 2 wherein said method is AC impedance.

4. A method according to claim 3, wherein said AC impedance is measured over a range of frequencies.

5. A method according to claim 3, wherein said AC impedance is measured by transient methods with AC signal perturbation superimposed upon a DC potential applied to an electrochemical cell.

6. A method according to claim 3, wherein said AC impedance is measured by impedance analyzer, lock-in amplifier, AC bridge, AC voltammetry, or combinations thereof.

7. A method according to claim 1 wherein the polarity of said manipulation electrodes is periodically alternated.

8. A method according to claim 1 wherein said immobilized probe molecules are immobilized with linker moieties.

9. A method according to claim 8 wherein said linker moieties comprise a conjugated polymer.

10. A method according to claim 9 wherein said conjugated polymer is chosen from the group consisting of polypyrrole, polythiphene, polyaniline, polyfuran, polypyridine, polycarbazole, polyphenylene, poly(phenylenvinylene), polyfluorene, and polyindole.

11. A method according to claim 9 wherein said conjugated polymer is polypyrrole.

12. A method according to claim 8 wherein said linker moieties comprise a neutral pyrrole matrix.

13. A method according to claim 1 wherein said substrate comprises an array of test site electrodes.

14. A method according to claim 1 or 13 wherein said immobilized probe molecules are oligonucleotides.

15. A method according to claim 1 or 13 wherein said target molecule is an oligonucleotide.

16. A method according to claim 1 wherein said immobilized probe molecules are antigens.

17. A method according to claim 1 wherein said immobilized probe molecules are peptides.

18. A method according to claim 1 wherein said immobilized probe molecules are proteins.

19. A method according to claim 1 wherein said target molecule is a protein.

20. A method according to claim 1 wherein said target molecule is an antibody.

* * * * *

UNITED STATES PATENT AND TRADEMARK OFFICE
CERTIFICATE OF CORRECTION

PATENT NO.     : 6,602,400 B1
DATED          : August 5, 2003
INVENTOR(S)    : Choong et al.

It is certified that error appears in the above-identified patent and that said Letters Patent is hereby corrected as shown below:

<u>Title page,</u>
Item [56], References Cited, U.S. PATENT DOCUMENTS, insert the following:
```
-- 5,952,172    09/1999     Meade, T., et al.
   6,087,100    07/2000     Meade, T., et al.
   6,090,933    07/2000     Kayyem, J., et al.
   6,096,273    08/2000     Kayyem, J., et al.
   6,132,683    10/2000     Sugihara, H., et al.
   6,177,250    01/2001     Meade, T., et al.
   6,180,352    01/2001     Meade, T., et al.
   6,200,761    03/2001     Meade, T., et al.
   6,221,583    04/2001     Kayyem, J., et al.
   6,232,062    05/2001     Kayyem, J., et al.
   6,238,870    05/2001     Meade, T., et al.
   6,258,545    07/2001     Meade, T., et al.
   6,268,149    07/2001     Meade, T., et al.
   6,268,150    07/2001     Meade, T., et al.
   6,277,576    08/2001     Meade, T., et al. --
```

FOREIGN PATENT DOCUMENTS, insert the following:
```
-- WO 95/15971   06/1995
   WO 96/40712   12/1996
   WO 97/46568   12/1997
   WO 98/12430   03/1998
   WO 98/20162   05/1998
   WO 98/57159   12/1998
   WO 01/42508   06/2001
   WO 01/57533   08/2001
   WO 01/61053   08/2001 --
```

UNITED STATES PATENT AND TRADEMARK OFFICE
CERTIFICATE OF CORRECTION

PATENT NO. : 6,602,400 B1
DATED : August 5, 2003
INVENTOR(S) : Choong et al.

It is certified that error appears in the above-identified patent and that said Letters Patent is hereby corrected as shown below:

<u>Title page cont'd,</u>
OTHER PUBLICATIONS, insert the following:
-- Sawyer, D., et al., <u>Electrochemistry for Chemists</u>, $2^{nd}$ ed. (1995), John Wiley & Sons, pp. 188-189. --

Signed and Sealed this

Ninth Day of December, 2003

JAMES E. ROGAN
*Director of the United States Patent and Trademark Office*